United States Patent [19]

Chamberlain

[11] Patent Number: 4,581,450
[45] Date of Patent: Apr. 8, 1986

[54] 3-HYDROXY-8-OXOQUINAZOLO[3,2-A]-QUINOLINES

[75] Inventor: Terence R. Chamberlain, Cincinnati, Ohio

[73] Assignee: Sun Chemical Corporation, New York, N.Y.

[21] Appl. No.: 673,121

[22] Filed: Nov. 19, 1984

Related U.S. Application Data

[62] Division of Ser. No. 542,019, Oct. 14, 1983, Pat. No. 4,508,899.

[51] Int. Cl.$^4$ ............................................. C07D 471/04
[52] U.S. Cl. .................................................... 544/246
[58] Field of Search ................................ 544/246, 225

[56] References Cited

U.S. PATENT DOCUMENTS 4,474,952  10/1984  Iqbal .................................. 544/225
4,508,899   2/1985  Chamberlain ..................... 544/225

OTHER PUBLICATIONS

Bose et al., Chemical Abstracts, vol. 26, 12863 (1932).
Zeide et al., Chemical Abstracts, vol. 32, 5723 (1938).
Stephen et al., Chemical Abstracts, vol. 51, 6647h-6649a (1957).

Khalifa et al., Chemical Abstracts, vol. 99, 175560d (1983).

Primary Examiner—Mark L. Berch
Assistant Examiner—Diana G. Rivers
Attorney, Agent, or Firm—Cynthia Berlow; Mitchell D. Bittman

[57] ABSTRACT

Pigments that can be used to color plastics, paints, and printing inks have the structural formula

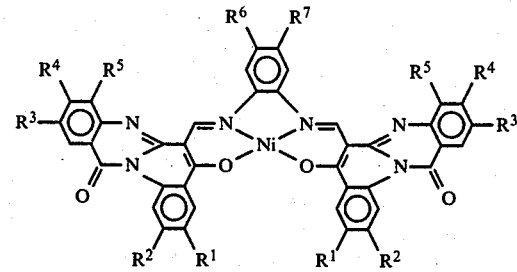

wherein each $R^1$, each $R^3$, and $R^7$ represent hydrogen, halogen, nitro, or lower alkyl and each $R^2$, each $R^4$, each $R^5$, and $R^6$ represent hydrogen or halogen.

6 Claims, No Drawings

3-HYDROXY-8-OXOQUINAZOLO[3,2-A]-QUINOLINES

This application is a division of application Ser. No. 542,019 filed Oct. 14, 1983 now U.S. Pat. No. 4,508,899.

This invention relates to metal complex pigments. More particularly, it relates to nickel complex pigments of bis-azomethines and to a process for making these pigments.

In accordance with this invention, it has been found that 1:1 nickel complex pigments of bis-azomethines can be used to color plastics, lacquers, and printing inks in yellow to orange shades and have outstanding fastness properties.

The novel pigments of this invention are nickel complexes of 1,2-phenylene-bis-(2-azomethinyl-3-hydroxy-8-oxoquinazolo-[3,2-a]-quinolines that have the structural formula

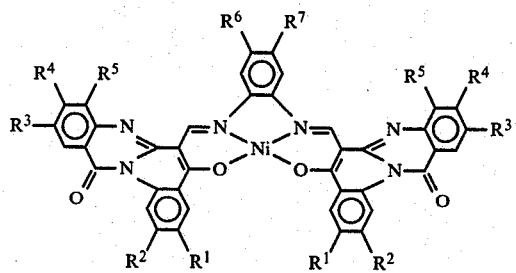

wherein each $R^1$, each $R^3$, and $R^7$ may represent hydrogen; halogen, that is, chlorine or bromine; nitro; or lower alkyl, that is, methyl, ethyl, propyl, or butyl; and each $R^2$, each $R^4$, each $R^5$, and $R^6$ may represent hydrogen or halogen.

While all of the nickel complexes are orange or yellow in color, the shade of the pigment is dependent upon the number of substituents, the nature of the substituents and the positions of the substituents on the rings of the complex.

In general, halogen- or alkyl-substituted pigments are redder in shade than the unsubstituted complex. The chloro-substituted products are usually stronger and cleaner pigments than the corresponding methyl-substituted products. As their chlorine content increases, the pigments become redder in shade. The bromine-substituted complexes tend to be redder in shade than the corresponding chloro-substituted complexes. When a single chlorine atom is introduced into the diamine bridge of the tetrabromo-complex, its shade becomes redder; when two chlorine atoms are introduced into the diamine bridge, a maroon pigment is obtained. Those complexes in which $R^3$ represents nitro are generally browner in tone than those in which the substituent in this position is chloro. When $R^6$ represents nitro, the complex is considerably redder in tone than the unsubstituted complex ($R^6$ equals H).

The nickel complex pigments of this invention may be prepared by a multistep process in which an N-(2-carboxyphenyl)-2-methyl-4-quinazolone is reacted with N-methylpyrrolidone and acetic anhydride to form a 3-hydroxy-8-oxoquinazolo[3,2-a]-quinoline, which is then reacted with ethyl N-phenylformimidate to form a phenyl azomethine. The phenyl azomethine is reacted with a diaminobenzene and a water-soluble nickel salt in an inert solvent to form the nickel complex.

The formation of the phenyl azomethine and the nickel complex are shown in the following equations:

Equation 1

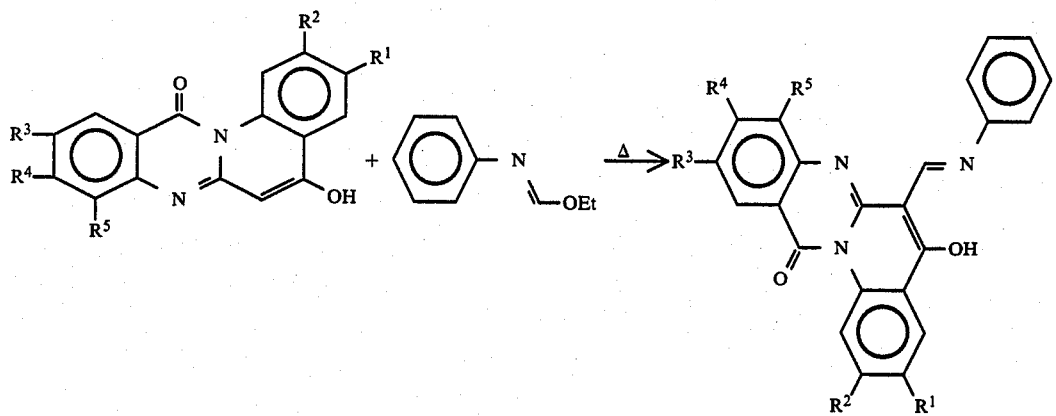

Equation 2

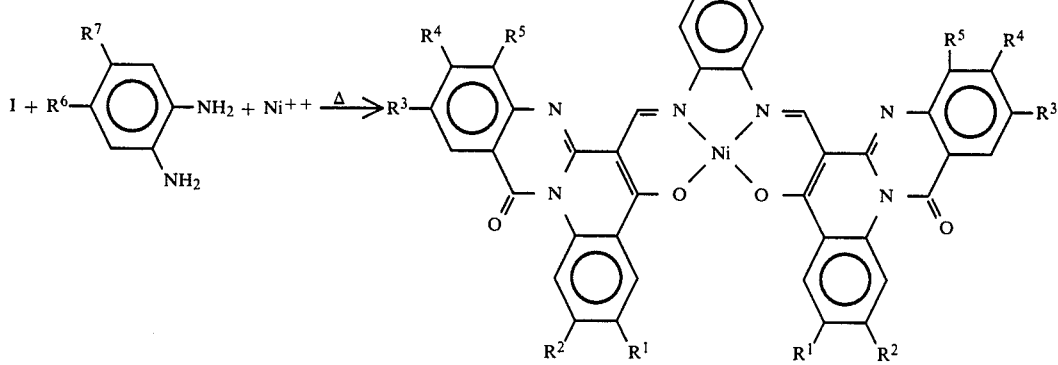

The N-(2-carboxyphenyl)-2-methyl-4-quinazolones that are used in the first step of this process are prepared from anthranilic acid or a substituted anthranilic acid by a process that is well known in the art. Among the substituted anthranilic acids that can be used are 5-chloroanthranilic acid, 6-chloroanthranilic acid, 4,6-dichloroanthranilic acid, 5-bromoanthranilic acid, 5-methylanthranilic acid, and the like, and mixtures thereof.

The N-(2-carboxyphenyl)-2-methyl-4-quinazolone is then heated with acetic anhydride and N-methylpyrrolidone or a solvent such as N,N-dimethylacetamide or N,N-dimethylformamide at the reflux temperature of the mixture to form a 3-hydroxy-8-oxoquinazolo-[3,2-a]-quinoline, which is recovered from the reaction mixture and air-dried.

This compound is then added to a reaction mixture obtained by heating aniline with triethylorthoformate and an acid catalyst that may be p-toluenesulfonic acid in N,N-dimethylacetamide at its reflux temperature until all of the byproduct ethanol was distilled off. The resulting mixture is heated at its reflux temperature to form a phenyl azomethine.

Simultaneous addition of 1,2-diaminobenzene or substituted 1,2-diaminobenzene, such as 1,2-diamino-4-bromobenzene, 1,2,-diamino-4-nitrobenzene, or 1,2-diamino-4,5-dichlorobenzene, a water-soluble nickel salt, and an inert solvent to the refluxing mixture results in the immediate precipitation of a colored product. This product is collected; washed with a hot solvent, such as dimethylformamide or dimethylacetamide, and then successively with water and acetone; and dried. The 1:1 nickel complexes that are obtained may be conditioned, for example, by ball milling with acetone, and then used to color polyethylene, polyvinyl chloride, and other thermoplastic resins; paints; and printing inks. These colored products exhibit very good light fastness, thermal stability, and resistance to migration.

The invention is further illustrated by the following examples:

EXAMPLE 1

(A) Preparation of 3-hydroxy-8-oxoquinazolo-[3,2-a]-quinoline

To a solution of 50 ml. (0.45 mole) of acetic anhydride and 60 ml. of N-methylpyrrolidone at 120°–130° C. was added with stirring 28 grams (0.1 mole) of finely-powdered N-(2-carboxyphenyl)-2-methyl-4-quinazolone, which had been prepared from anthranilic acid and acetic anhydride by a conventional process. The resulting solution was heated at its reflux temperature for 5 hours. After the addition of 10 ml. of water, the reaction mixture was heated at its reflux temperature for 1 hour and then cooled and filtered. The filter residue was washed well with acetone and air-dried. There was obtained 18.4 grams (70.2% of theory) of a beige solid which melted at 301° C. The structure of the product was confirmed by analysis.

(B) Preparation of the nickel (2) Complex of 1,2-phenylene-bis-(2-azomethinyl-3-hydroxy-8-oxoquinazolo-[3,2-a]-quinoline)

To a stirred solution of 14.8 ml. (0.089 mole) of triethylorthoformate and 0.2 gram of p-toluenesulfonic acid in 100 ml of N,N-dimethylacetamide which had been heated to 100°–120° C. was added 8.1 ml. (0.089 mole) of aniline over a period of 10 minutes. After the byproduct ethanol had been distilled off, the solution was heated at its reflux temperature for 1 hour. Then 15.5 grams (0.059 mole) of the product of part (A) was added to the solution in 10 minutes, and the resulting solution was heated at its reflux temperature for 1 hour.

Simultaneous addition of 6.5 grams (0.06 mole) of 1,2-diaminobenzene, 8.6 grams (0.03 mole) of nickel nitrate.6H$_2$O, and 4.9 grams (0.06 mole) of sodium acetate to the refluxing solution resulted in the immediate precipitation of a red-yellow solid. The resulting suspension was heated at its reflux temperature for 1 hour and then filtered hot. The filter residue was washed thoroughly with dimethylacetamide and then successively with water and acetone, and dried. There was obtained 13.3 grams (58% of theory) of the nickel (2) complex, which was a reddish-yellow solid that had a molecular weight of 708.7 and that was found by microanalysis to contain 67.83% C, 3.23% H, 11.84% N, and 8.08% Ni (calculated: 67.73% C, 3.10% H, 11.85% N, and 8.28% Ni).

(C) To 100 grams of granular polyethylene was added 0.2 gram of the pigment of part (B). The mixture was injection molded at 280°–300° C. to form pigmented chips. The red-shade tan chips exhibited very good fastness to light and migration.

EXAMPLE 2

Preparation of the nickel (2) complex of 1,2-phenylene-bis-(2-azomethinyl-3-hydroxy-6,11-dichloro-8-oxoquinazolo-[3,2-a]-quinoline To a stirred solution of 34.9 ml. (0.21 mole) of triethylorthoformate and 0.5 gram of p-toluenesulfonic acid in 60 ml. of 1,2-dichlorobenzene which has been heated to 100°–120° C. was added with stirring 19.1 ml. (0.21 mole) of aniline over a period of 10 minutes. After the byproduct ethanol had been distilled off, the solution was heated at its reflux temperature for 1 hour. Then 45.2 grams (0.137 mole) of finely-powdered 3-hydroxy-6,11-dichloro-8-oxoquinazolo-[3,2-a]-quinoline was added to the solution over a period of 15 minutes; the resulting mixture was heated at its reflux temperature for 2 hours and then cooled. The mixture was filtered, and the collected solid product was washed thoroughly, first with toluene and then with ligroine (60°–90° C.); and air-dried. There was obtained 47 grams (79% of theory) of a bright yellow phenyl azomethine that melted at 270°–273° C. and had the structural formula

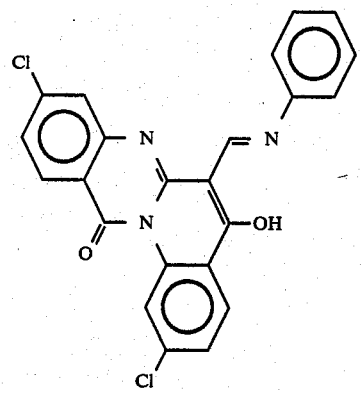

When a slurry of 6.6 grams (0.06 mole) of 1,2-diaminobenzene and 15 grams (0.06 mole) of nickel acetate.4H$_2$O in 100 ml. of dimethylformamide was added to an efficiently agitated mixture of 47 grams (0.11 mole) of the phenyl azomethine in 1300 ml. of dimethylformamide at its reflux temperature, an orange-red precipitate formed immediately. After 2 hours at its reflux temperature, the reaction mixture was filtered hot. The filter residue was washed thoroughly with hot dimethylformamide and then with water and acetone; and then dried. There was obtained 45.8 grams (92% of theory) of the orange nickel (2) complex of 1,2-phenylene-bis-(2-azomethinyl-3-hydroxy-6,11-dichloro-8-oxoquinazolo-[3,2-a]-quinoline) that had a molecular weight of 846.7 and that was found by microanalysis to contain 56.56% C, 2.48% H, 16.56% Cl, 9.87% N, and 7.10% Ni (calculated: 56.69% C, 2.13% H, 16.77% Cl, 9.92% N, and 6.93% Ni).

The product was dispersed in thermoplastic acrylic lacquer paint by ball milling. A portion of the paint was extended with sufficient titanium dioxide to give a final toner to white ratio of 5 to 95, and the two paints were sprayed onto primer-coated aluminum panels. In each case, an orange finish of very good fastness to overstripe bleeding, light, and atmospheric influences was obtained.

EXAMPLES 3–23

Using the procedure of Example 1 and the appropriate 3-hydroxy-8-oxoquinazolo-[3,2-a]-quinolines, ethyl N-phenylformimidate and diaminobenzenes, a series of nickel complexes was prepared. The structures of these pigments and their colors are shown in the following table:

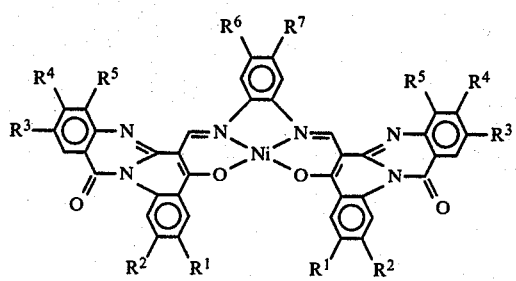

TABLE

| Example No. | R$^1$ | R$^2$ | R$^3$ | R$^4$ | R$^5$ | R$^6$ | R$^7$ | Color |
|---|---|---|---|---|---|---|---|---|
| 3 | H | Cl | H | Cl | H | H | H | orange |
| 4 | Cl | H | H | Cl | H | H | H | orange |
| 5 | Cl | H | Cl | H | H | H | H | orange |
| 6 | H | Cl | Cl | H | H | H | H | orange |
| 7 | H | Cl | H | H | H | H | H | red-yellow |
| 8 | Cl | H | H | H | H | H | H | yellow-orange |
| 9 | H | H | Cl | H | H | H | H | yellow-orange |
| 10 | H | Cl | Cl | H | Cl | H | H | red-orange |
| 11 | H | Cl | Br | H | Br | H | H | red-yellow |
| 12 | CH$_3$ | H | H | H | H | H | H | yellow-orange |
| 13 | H | H | CH$_3$ | H | H | H | H | yellow-orange |
| 14 | CH$_3$ | H | CH$_3$ | H | H | H | H | yellow-orange |
| 15 | H | Cl | H | Cl | H | Cl | Cl | red-orange |
| 16 | H | H | H | H | H | Cl | H | yellow-orange |
| 17 | H | H | NO$_2$ | H | H | H | H | brownish-orange |
| 18 | H | H | H | H | H | H | NO$_2$ | red-orange |
| 19 | Br | H | Br | H | H | H | H | red-orange |
| 20 | Br | H | Br | H | H | Cl | H | red-orange |
| 21 | Br | H | Br | H | H | Cl | Cl | maroon |
| 22 | H | H | Br | H | H | H | H | orange |
| 23 | H | H | Br | H | H | Cl | H | red-orange |

What is claimed is:

1. A 3-hydroxy-8-oxoquinazolo-[3,2-a]-quinoline having the structural formula

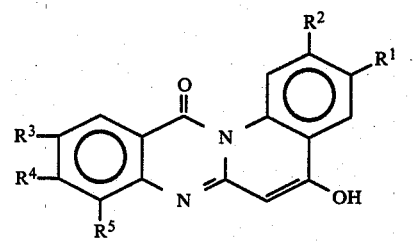

wherein R$^1$ and R$^3$ represent hydrogen, halogen, nitro, or lower alkyl and R$^2$, R$^4$, and R$^5$ represent hydrogen or halogen.

2. The compound of claim 1 wherein R$^1$ and R$^4$ represent hydrogen and R$^2$, R$^3$, and R$^5$ represent chlorine.

3. The compound of claim 1 wherein R$^1$, R$^3$, and R$^5$ represent hydrogen and R$^2$ and R$^4$ represent chlorine.

4. The compound of claim 1 wherein R$^1$ and R$^4$ represent hydrogen; R$^2$ represents chlorine; and R$^3$ and R$^5$ represent bromine.

5. The compound of claim 1 wherein R$^1$ and R$^3$ represent methyl and R$^2$, R$^4$, and R$^5$ represent hydrogen.

6. The compound of claim 1 wherein R$^1$ through R$^5$ represent hydrogen.

* * * * *